(12) United States Patent
Haemmerich et al.

(10) Patent No.: US 8,419,725 B2
(45) Date of Patent: Apr. 16, 2013

(54) METHOD AND DEVICES FOR CARDIAC RADIOFREQUENCY CATHETER ABLATION

(75) Inventors: Dieter Haemmerich, Charleston, SC (US); J. Philip Saul, Mt. Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 13/096,136

(22) Filed: Apr. 28, 2011

(65) Prior Publication Data

US 2011/0264087 A1    Oct. 27, 2011

Related U.S. Application Data

(63) Continuation of application No. 11/467,590, filed on Aug. 28, 2006, now abandoned.

(60) Provisional application No. 60/711,742, filed on Aug. 26, 2005.

(51) Int. Cl.
*A61B 18/12* (2006.01)

(52) U.S. Cl.
USPC .......................................................... 606/32

(58) Field of Classification Search .......... 606/32–50; 607/96–102, 113, 122; 128/898
See application file for complete search history.

(56) References Cited

U.S. PATENT DOCUMENTS

| | | | |
|---|---|---|---|
| 4,576,182 A | 3/1986 | Normann | |
| 5,174,299 A | 12/1992 | Nelson | |
| 5,233,515 A | 8/1993 | Cosman | |
| 5,557,967 A | 9/1996 | Renger | |
| 5,782,879 A | 7/1998 | Rosborough et al. | |
| 5,836,990 A * | 11/1998 | Li | 607/28 |
| 5,917,980 A | 6/1999 | Yoshimura et al. | |
| 6,049,737 A | 4/2000 | Simpson et al. | |
| 6,063,078 A * | 5/2000 | Wittkampf | 606/41 |
| 6,162,184 A | 12/2000 | Swanson et al. | |
| 6,197,023 B1 | 3/2001 | Muntermann | |
| 6,217,573 B1 | 4/2001 | Webster | |
| 6,293,943 B1 * | 9/2001 | Panescu et al. | 606/41 |
| 6,322,558 B1 * | 11/2001 | Taylor et al. | 606/34 |
| 6,391,024 B1 | 5/2002 | Sun et al. | |
| 6,569,160 B1 * | 5/2003 | Goldin et al. | 606/41 |
| 6,666,862 B2 * | 12/2003 | Jain et al. | 606/41 |
| 6,696,844 B2 * | 2/2004 | Wong et al. | 324/693 |
| 7,008,417 B2 * | 3/2006 | Eick | 606/41 |
| 7,306,593 B2 * | 12/2007 | Keidar et al. | 606/34 |
| 2006/0235314 A1 | 10/2006 | Migliuolo et al. | |

OTHER PUBLICATIONS

Shah J. Instrument to measure the heat convection coefficient on the endothelial surface of arteries and veins. Medical & Biological Engineering & Computing [serial online]. Jul. 2005;43(4):522-527. Available from: Computer Source, Ipswich, MA. Accessed Apr. 19, 2012.*

(Continued)

*Primary Examiner* — Michael Peffley
*Assistant Examiner* — Ronald Hupczey, Jr.
(74) *Attorney, Agent, or Firm* — Barnwell Whaley Patterson & Helms, LLC

(57) ABSTRACT

Embodiments of the invention comprise methods and devices that allow quantification of blood convective cooling at the cardiac RF catheter ablation site and allow for prediction of lesion size and/or computation of RF energy parameters and characteristics.

10 Claims, 8 Drawing Sheets

OTHER PUBLICATIONS

H. Cao, et al. Flow Effect on lesion formation of RF cardiac catheter ablation, IEEE Trans. Biomed Eng. vol. 48, pp. 425-433, 2001.

R. Mukherjee, P. et al., "Counter Intuitive relations between in vivo RF lesion size, power, and tip temperature", J. Interv. Card. Electrophysiol, vol. 9., pp. 309-315, 2003.

H.H. Petersen, et al., "Lesion dimensions during temperature-controlled radiofrequency catheter ablation of left ventricular porcine myocardium: impact of ablation site, electrode size and convective cooling, ", Circulation, vol. 99, pp. 319-325, 1999.

Tungjitkusolmun, et al. "Guidelines for predicting lesion size at common endocardial locations during radio-frequency ablation,", IEEE Trans Biomed, Eng. vol. 48, pp. 194-201, 2001.

Lai, et al. "Lesion size estimator of cardiac radiofrequency ablation at different common locations with different tip temperatures.", IEEE Trans Biomed. Eng., vol. 51, pp. 1859-1864, 2004.

Jain, et al., "A three-dimensional finite element model of radiofrequency ablation with blood flow and its experimental validation." Ann Biomed. Eng., vol. 28, pp. 1075-1084, 2000.

Labonte, Numerical model for radio-frequency ablation of the endocardium and its experimental validation, IEEE, Trans Biomed Eng. vol. 41, pp. 108-115, 1994.

Nath, et al. "Cellular electrophysiological effects of hyperthermia on isolated guinea pig papillary muscle. Implication for catheter abalation". Circulation vol. 88, pp. 1825-1831, 1993.

Haines, et al., "Tissue heating during radiofrequency catheter ablation: a thermodynamic model and observations in isolated perfused and superfused canine right venticular free wall." Pacing Clin. Electrophysiol. vol. 12, pp. 962-976, 1989.

Haines, et al., "Tissue heating during radiofrequency catheter ablation: a thermodynamic model and observations in isolated perfused and superfused canine right ventricular free wall." Pacing Clin Electrophysiol, vol. 12, pp. 962-976, 1989.

Tsai, et al. "In-vivo measurement of swine myocardial resistivity", IEEE Trans Biomed Eng. vol. 17, pp. 25-104, 1989.

Tsai, et al. "In-vivo measurement of swine myocardial resistivity", IEEE Trans Biomed, Eng., vol. 49, pp. 472-483, 2002.

Foster, et al. "Dielectric properties of tissues and biological materials: a critical review." Crit. Rev. Biomed Eng., vol. 17, pp. 25-104, 1989.

Tungjitkusolmun, et al., "Using electrical impedance to predict catheter-endocardial contact during RF cardiac ablation," J. Cardiovasc. Electrophysiol.

Eick, et al. "The LETR-Principle: a novel method to assess electrode-tissue contact in radiofrequency ablation." J. Cardiovasc. Electrophysiol, vol. 9, pp. 1180-1185, 1998.

J. M. Kalman, A. P. Fitzpatrick, J. E. Olgin, M. C. Chin, R. J. Lee, M. M. Scheinman, and M. D. Lesh, "Biophysical characteristics of radiofrequency lesion formation in vivo: dynamics of catheter tip-tissue contact evaluated by intracardiac echocardiography," Am. Heart J., vol. 133, pp. 8-18, 1997.

Petersen, et al, "Can Lesion Size During Radiofrequency Ablation Be Predicted by the Temperature Rise to a Low Power Test Pulse in Vitro", PACE, vol. 26, pp. 1653-1659, 2003.

Eick, PhD, "Factors Influencing Lesion Formation During Radiofrequency Catheter Ablation", Indian Pacing and Electrophysiology Journal, ISSN 0972-6292, pp. 117-128, 2003.

* cited by examiner

| FlowRate (L/min) | Electrode Temp. (°C) | Power (W) | Impedance (Ohms) | Depth (mm) | Width (mm) | Volume (mm³) |
|---|---|---|---|---|---|---|
| | Avg±StDew | Avg±StDew | Avg±StDew | Avg±StDew | Avg±StDew | Avg±StDew |
| 0 | 62.9±0.2 | 24.4±5.1 | 74.6±2.7 | 4.5±0.5 | 6.8±1.1 | 120.7±50.7 |
| 1 | 62.4±0.4 | 32.6±5.2 | 75.8±1.3 | 5.8±0.8 | 8.8±1.2 | 256.5±97.9 |
| 2 | 61.9±0.5 | 49.7±10.9 | 74.6±1.7 | 7.0±1.1 | 9.8±1.6 | 393.4±149.9 |
| 3 | 61.9±0.6 | 51.7±11.1 | 74.4±1.3 | 7.6±0.9 | 11.3±1.2 | 548.9±157.0 |

Table 1

FIG. 10

| Approximation According To: | dTmax | | slope | |
|---|---|---|---|---|
| | Depth | Width | Depth | Width |
| Average error | 0.7 mm (11.2%) | 1.1 mm (13.3%) | 0.78 mm (13.0%) | 1.22 mm (14.4%) |
| Maximum error | 1.8 mm (33.0%) | 2.52 mm (34.7%) | 2.07 mm (40.2%) | 2.76 mm (35.6%) |

Table 2

FIG. 11

| Parameter | Flow rates compared | P-value |
|---|---|---|
| Depth | 0,1<br>1,2<br>2,3 | <0.005*<br><0.005*<br>0.29 |
| Width | 0,1<br>1,2<br>2,3 | <0.0001*<br>0.12<br>0.05* |
| Volume | 0,1<br>1,2<br>2,3 | <0.005*<br><0.005*<br><0.05* |

Table 3

FIG. 12

METHOD AND DEVICES FOR CARDIAC RADIOFREQUENCY CATHETER ABLATION

CROSS REFERENCE TO RELATED APPLICATIONS

This application is a continuation of patent application Ser. No. 11/467,590, filed Aug. 28, 2006, now abandoned, which claimed the benefit of Provisional Patent Application entitled "Quantification of Local Convectional Cooling During Cardiac Radiofrequency Catheter Ablation", by Haemmerich and Saul, Ser. No. 60/711,742 filed on Aug. 26, 2005, and hereby incorporated by reference as if rewritten in full.

BACKGROUND OF THE INVENTION

Radiofrequency (RF) ablation is a medical procedure which can be used to treat some types of rapid heart beating including conditions such as supraventricular tachyarrhythmias. Ablation can be used to treat a wide variety of tachycardias, which can involve heart tissues in the upper chambers (atria), also called supraventricular, or the lower chambers (ventricles), called ventricular tachycardias (SVT or VT). In some cases, a small number of cells (a "focus") start firing rapidly and ablation can eliminate the focus. In other types of tachycardia, an electrical circuit exists within which the electrical signal travels more or less in a circle ("reentry"). Many cases of SVT and VT are due to reentry. A special type of SVT, called atrial fibrillation, is characterized by extremely fast impulses in the atrium (up to 600/min), for which ablation can be used either to decrease the number of impulses getting to the ventricles or in some cases to locate and ablate the area(s) from which the fibrillation starts. (*Circulation.* 2002; 106:e203.)

An example of an ablation procedure is as follows: A physician guides a catheter with an electrode at its tip to the area of heart muscle where there's an accessory (extra) pathway. The catheter is guided with real-time, moving X-rays (fluoroscopy) displayed on a video screen. The procedure helps the doctor place the catheter at the exact site inside the heart where cells give off the electrical signals that stimulate the abnormal heart rhythm. Then a mild, radiofrequency energy (similar to microwave heat) is transmitted to the pathway. This destroys carefully selected heart muscle cells in a very small area (about ⅕ of an inch). That stops the area from conducting the extra impulses that caused the rapid heartbeats.

Radiofrequency current can be alternating current that is delivered at cycle lengths of 300 to 750 kHz when used for catheter ablation. It causes resistive heating of the tissue in contact with the electrode. Because the degree of tissue heating is inversely proportional to the radius to the fourth power, the lesions created by radiofrequency energy are small. Typical ablation catheters, which are 2.2 mm in diameter (7 French) and have a distal electrode 4 mm long, create lesions approximately 5 to 6 mm in diameter and 2 to 3 mm deep. Larger lesions are possible with larger electrodes or saline-irrigated ablation catheters. Although electrical injury may be a contributing factor, the primary mechanism of tissue destruction by radiofrequency current is thermal injury. Irreversible tissue destruction can require a tissue temperature of approximately 50° C. In most ablation procedures, the power output of the radiofrequency generator is adjusted manually or automatically to achieve a temperature of 60 to 75° C. at the electrode-tissue interface. If the temperature at the electrode-tissue interface reaches about 100° C., coagulated plasma and desiccated tissue may form on the electrode, preventing effective delivery of the current, predisposing the patient to thromboembolic complications, and necessitating the removal of the catheter so that the coagulated material can be wiped off the electrode. The acute lesion created by radiofrequency can consist of a central zone of coagulation necrosis surrounded by a zone of hemorrhage and inflammation. Chronic lesions are often characterized by coagulation necrosis and have a discrete border. Changes that occur in the border zone can explain why arrhythmias may recur several days to several weeks after apparently successful ablation. The arrhythmia may recur if the target tissue is in the zone bordering a lesion instead of in the central area of necrosis and if the inflammation resolves without residual necrosis. Conversely, the site of origin of an arrhythmia that has not been successfully ablated may later become permanently nonfunctional if it is within the border zone of a lesion and if microvascular injury and inflammation within this zone result in progressive necrosis. (New England J of Medicine, Volume 340:534-544, Feb. 18, 1999).

BRIEF SUMMARY OF THE INVENTION

Embodiments of the invention comprise methods for computing convection cooling parameters associated with the site for the application of RF ablation. Additional embodiments of the invention comprise devices for the control of cardiac RF ablation. Further embodiments of the invention comprise computer readable medium capable of execution in a computer or other processing unit whereby an ablation lesion size is predicted based upon the input of certain parameters or measurements. Parameters can be such things as temperature measured at the electrode tip of a catheter while the catheter is energized with RF energy. Other parameters can be temperature measured at the electrode tip of a catheter for a fixed time period after the application of RF energy to the catheter. Parameters can also be those known to one of ordinary skill in the art that characterize the RF energy applied to the tip, including frequency, pulse shape, pulse duration, magnitude, and temperature of the tip.

BRIEF DESCRIPTION OF THE DRAWINGS

FIG. 10, Table 1. Temperature, Power, Impedance, and lesion dimensions at different flow rates.

FIG. 11, Table 2. Absolute (mm) and relative error (%) of lesion width and depth predicted by parameters dTmax, and slope using linear regression equations.

FIG. 12, Table 3. t-test: comparison of lesion dimensions at different flow rates.

DETAILED DESCRIPTION OF THE INVENTION

Cardiac radiofrequency (RF) catheter ablation has become the treatment of choice for a wide array of both supraventricular and ventricular arrhythmia. The dimensions of the lesion created during RF ablation depend on several factors such as catheter geometry, catheter-endocardial contact, and blood flow. Several studies examined the dependence of lesion size on blood flow [1-4]. Convective cooling by the blood carries away heat from the catheter tip and endocardium, enabling deposition of more RF energy deeper into the tissue. When RF power is not limited, higher blood flow can result in wider and deeper RF lesions. These results have been shown in ex vivo experiments [1, 3] and computer models [4, 5]. Similarly, in vivo experiments in a porcine animal model have shown that ablation site within the heart affects lesion size. Mukherjee, et al., classified different ablation sites in the endocardium according to flow conditions (low/medium/high), and found significant differences in lesion size depending on ablation site [2].

Embodiments of the invention present two methods to quantify convective cooling at the ablation site before cardiac RF catheter ablation is performed. These methods can be used to directly predict lesion size at the ablation site. Quantitative data on convective cooling can also be used as input parameters for computer models [4-7] in order to more-accurately estimate lesion size and include this information in treatment planning.

Figure 1:
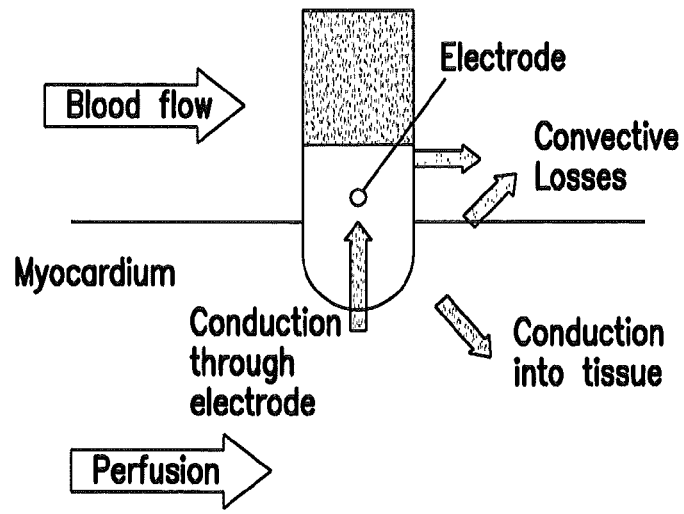
FIG. 1. Heat transfer mechanisms during RF ablation.

While RF energy is applied, heat is transferred to and from the tissue, simultaneously, by several different mechanisms (see FIG. 1). The RF current causes resistive heating of the myocardium close to the catheter. Heat energy is conducted into the myocardium, which elevates tissue temperature, resulting in a lesion once temperatures exceed ~50° C. [8]. However, lesion size is also affected by heat removal. In the myocardium, heat is lost due to blood perfusion. In addition, some heat from the electrode is conducted directly to the electrode surface in direct contact with the blood. Finally, endocardial convective cooling by the blood flow carries heat away from the electrode and endocardial surface.

The equations describing this heat transfer process in the tissue are:

$$\rho c \frac{\partial T}{\partial t} = \nabla \cdot k \nabla T + Q_{RF} - Q_{Perf} \quad (1)$$

T tissue temperature (° C.)
$\rho$ tissue density (kg/m$^3$)
c tissue specific heat (J/(kg K))
k tissue thermal conductivity (W/(m K))
$Q_{RF}$ power density deposited by RF current (W/m$^3$)
$Q_{Perf}$ energy removed by blood perfusion (W/m$^3$)

$$q''_{conv} = h(T - T_{Blood}) \quad (2)$$

$q''_{conv}$ Heat flux lost due to convection (W/m$^2$)
h convective heat transfer coefficient (W/(m$^2$ K))
T surface temperature (of endocardium/catheter)
$T_{Blood}$ temperature of blood Equation 1 describes the conductive heat transfer in the tissue. Blood perfusion ($Q_{perf}$) can be neglected, since it is small compared to the other terms [9]. Equation 2 describes the heat flux ($q''_{conv}$) removed by convection from the surfaces of catheter and endocardium. The heat transfer coefficient (h) is dependent on location (catheter, tissue), and blood flow [4]. An embodiment of the invention quantifies convective cooling by applying a short pulse of RF energy, and examining the resultant change in electrode temperature (monitored by a thermistor in the electrode). After RF power is turned off, electrode temperature will drop due to thermal conduction (Eq 1), and due to convective losses (Eq 2). Since tissue is a comparatively bad thermal conductor, we assume that the convective losses will dominate, allowing us quantification of these losses by examination of the dynamics of the electrode temperature drop.

From equations 1 and 2 we notice that the only absolute temperature present is Tblood (blood temperature, which is equal to initial tissue temperature). If we measure parameters relative to $T_{blood}$, we can avoid introducing errors as a result of variations in $T_{blood}$ (e.g. different body temperatures in different patients).

The following two parameters were measured following a brief RF pulse (see FIG. 2):
 maximum electrode temperature change ($dT_{max} = T_{max} - T_{blood}$) during application of constant power for specific time
 slope of temperature decay at 5° C. above $$T_{blood}\left(sl = \frac{\partial T}{\partial t}\bigg|_{Tblood+5° C.}\right),$$

after application of constant power

The accuracy of the measurement will be higher with increasing $T_{max}$, but to avoid damage to myocardium during measurement of convective cooling, the maximum temperature obtained during the RF pulse can be below approximately 50° C. [8].

The catheter can have a thermocouple, thermistor, or other temperature measuring means adjacent to or near the electrode tip of the catheter. The temperature measuring means can be located within the catheter including within the tip. The temperature measuring means are generally known to one of ordinary skill in the art.

RF energy for the catheter is generated using means known to one of ordinary skill in the art. Control of that RF energy can be done using means known to one of ordinary skill in the art. Control of the RF energy can comprise a digital control signal that is used to control an RF energy generator or transmitter. That control signal can also be used as an input into a processing unit that performs some of the methods of embodiments of the invention. Thus RF energy parameters such as pulse shape, pulse duration, pulse magnitude, and the like can be provided to the processing unit for inclusion in the convection cooling parameter generation and/or lesion size estimation. Further embodiments of the invention can include generation of a lesion size estimate based upon information inputted into a processing unit wherein the information comprises such things as the RF energy control parameters and the temperature measurements described herein.

Embodiments of the invention can include a processing unit wherein the processing unit is a personal computer such as a Windows based, or Linux based, PC generally known to one of ordinary skill in the art. The processing unit can also comprise a CPU, microcontroller, BASICstamp or similar device or apparatus for the performance of executable instructions that carry out the methodology of embodiments of the invention described herein. Storage media, communication media, and other input and output devices generally known to one of ordinary skill in the art can be used in embodiments of the invention. Processing means can be included within the devices and apparatus currently known in the art for performing cardiac catheter ablation but which do not incorporate embodiments of the invention described herein.

Experimental Results

Lesion sizes obtained during cardiac radiofrequency (RF) catheter ablation are dependent on convective cooling mediated by blood flow in the heart. For temperature controlled catheters, larger lesions can be obtained at locations with high blood flow. We performed ex vivo ablation experiments in porcine cardiac tissue in a saline bath with flow of varying flow rates (0, 1, 2, 3 L/min) directed over the ablation site. We investigated whether catheter tip temperature change following a brief low-power RF pulse can be used to predict lesion dimensions. Before the ablation procedure, we applied a pulse of constant power (15 W) for five seconds, and a pulse of varying time length and constant power (30 W) until electrode temperature reached 43° C. We determined maximum tip temperature change (dTmax) and the slope of tip temperature decay at 5° C. above initial temperature (slope). We correlated these two parameters with flow rate and lesion dimensions. Lesion dimensions varied significantly with flow rate. Without flow (0 L/min), lesion depth, width and volume were 4.5±0.5 mm, 6.8±1.1 mm, and 120.7±50.7 mm3, respectively. At maximum flow (3 L/min), lesion depth, width and volume were 7.6±0.9 mm, 11.3±1.2 mm and 548.9±157.0 mm3, respectively. dTmax showed strong negative correlation with lesion width ($r2=0.68$), depth ($r2=0.57$), and volume ($r2=0.56$); slope also correlated negatively and strongly with lesion width ($r2=0.62$), depth ($r2=0.52$), and volume ($r2=0.51$). Both parameters can be used to predict lesion dimensions depending on local blood flow at the treatment site.

Figure 3:
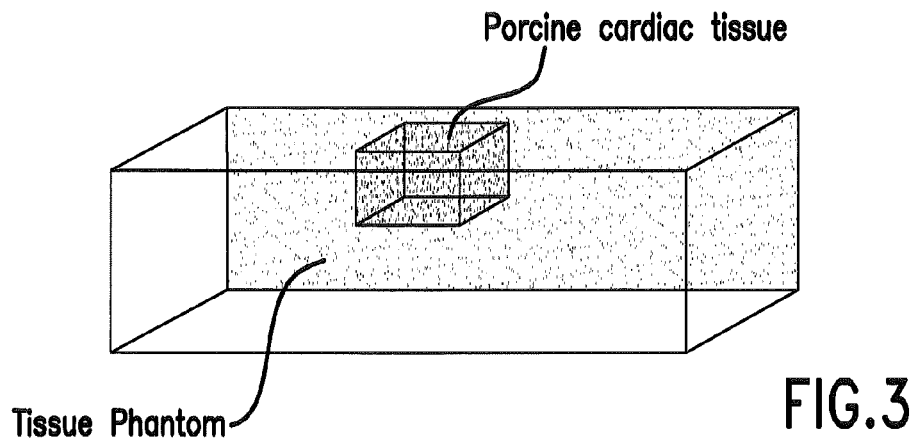
FIG. 3. Schematics of Tissue-Phantom Setup.

We used freshly-excised porcine heart obtained from a local butcher. Upon excision, the hearts were infused with chilled physiological saline (0.9% NaCl) for transport. The porcine hearts were dissected to create square pieces of myocardium (~20×20 mm, ~15 mm thick). This tissue sample was then placed in a gel block made of Agar-Water (5 mass % Agar) (see FIG. 3). The gel block was created to possess the same electrical conductivity as human myocardium at 500 kHz (0.54 S/m) [10]. The gel block mimicked surrounding myocardial tissue as it would be experienced in vivo. See FIG. 3

Figure 4:
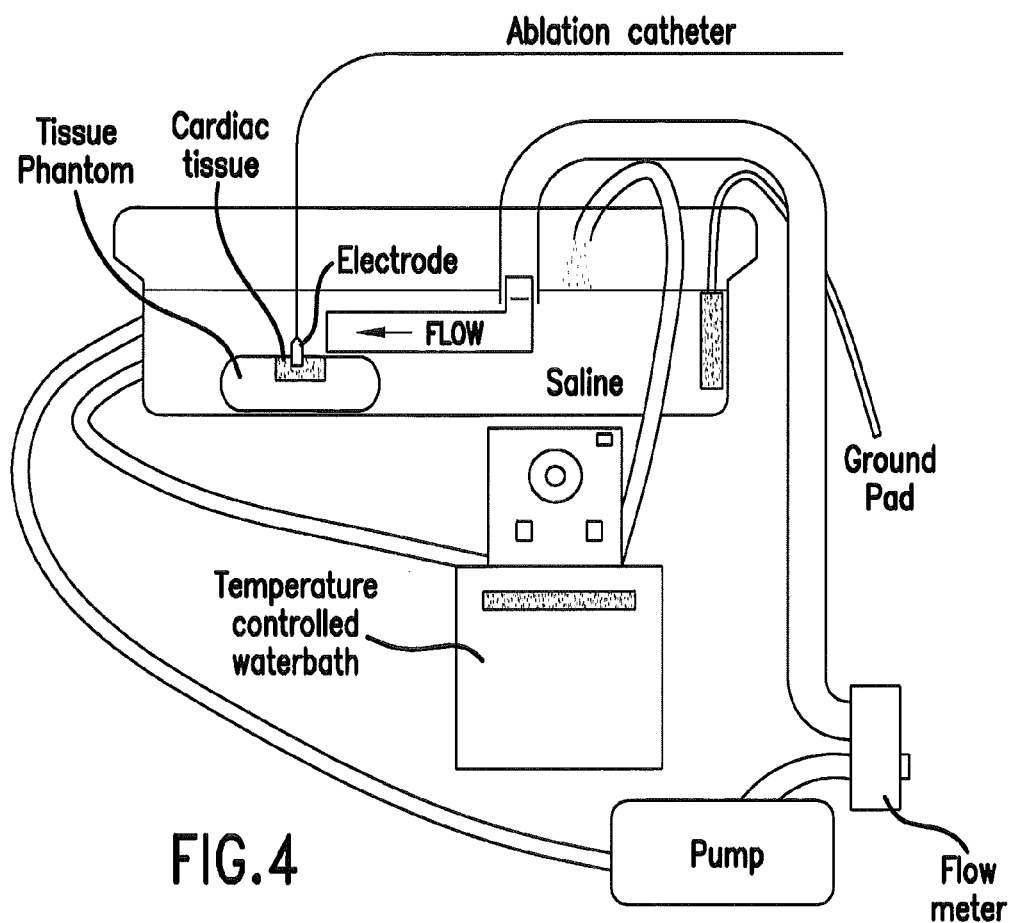
FIG. 4. Schematics of flow rig.

We immersed the gel block with tissue in 0.3% saline having same thermophysical properties as blood (0.67 S/m) at 37° C. and 500 kHz [11] (see FIG. 4). A temperature-controlled water bath (Haake C1, Haake, Offenburg, Germany) was used to maintain the saline temperature at 37±0.2° C. Blood flow was simulated by directing saline flow from a pump over the ablation site with a rigid Polyethylene tube (20 mm inner diameter). The cross-sectional area of the tubing reflects that of the mitral and tricuspid valves of the human heart. The amount of flow (flow rate) was controlled by a flow meter (Model 7200, King Instrument, 3% accuracy) attached to the pump. The saline was circulated to and from the pump by inflow and outflow plastic tubing, respectively.

We measured maximum flow velocity at different flow rates by injecting a droplet of dye at the inlet of the rigid tube and recording the wavefront at the phantom surface with a digital camera at 30 frames/s. Maximum flow velocity was found to be 15.5 cm/s at 3 L/min flow rate, This velocity is comparable to blood flow velocities inside the beating heart as measured by an ultrasound Doppler transducer [3]. The catheter was placed centered on the tissue sample, perpendicular to the endocardial surface. To control pressure between catheter and tissue, a 10 gram piece of Copper was attached to the neck of the catheter. Power was supplied to the RF ablation catheter by a commercial cardiac ablation generator (Boston Scientific, EPT-1000XP). The electrode of the catheter (Blazer II XP) was 10 mm long and 8 FR (2.7 mm) in diameter. As grounding pad we used a piece of aluminum foil (15×10 cm) placed in the saline bath, more than 20 cm distant from the ablation electrode.

Figure 5:
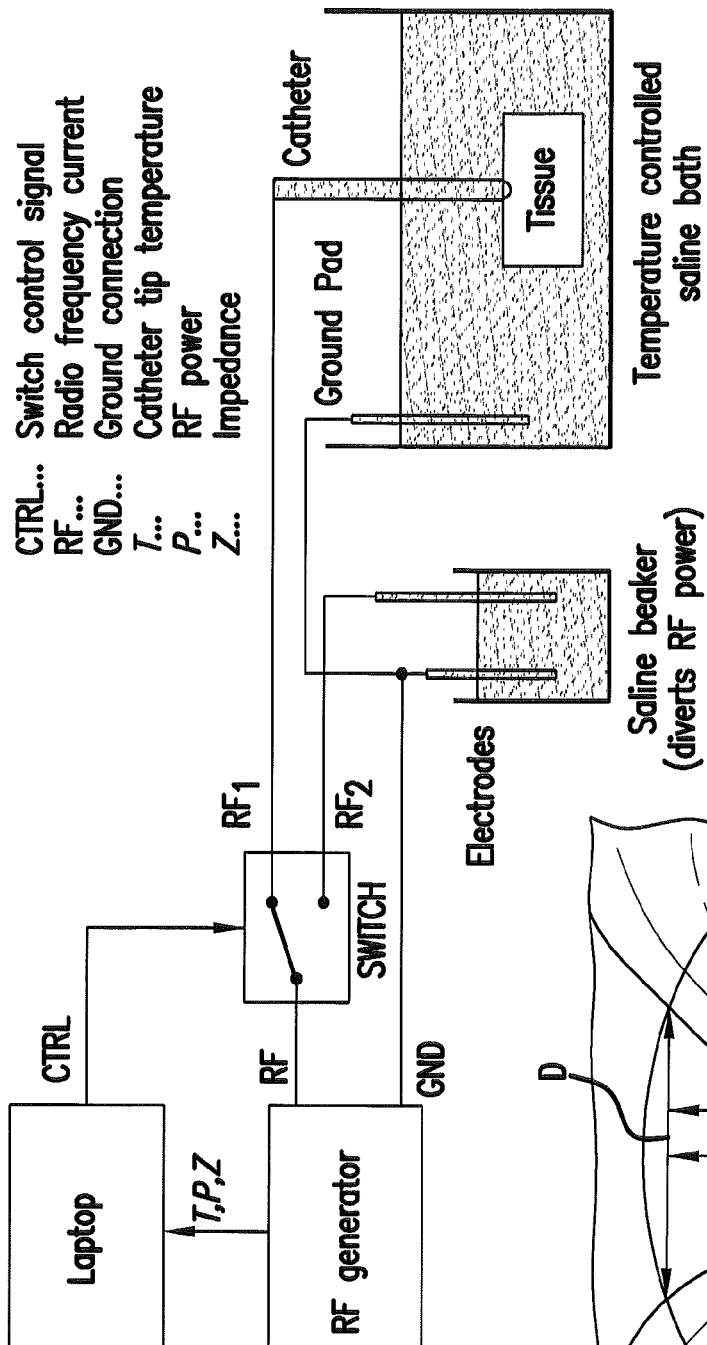
FIG. 5. Schematic of electrical system setup. The laptop controls the switch, which relays RF current to either the saline beaker, or the ablation catheter.

FIG. 5 shows the electrical system setup. A switch (electromagnetic relay) allowed relaying of RF current to either an electrode immersed in a beaker filled with saline, or to the ablation catheter. The switch was controlled via laptop. Temperature (T), RF power (P) and impedance (Z) were recorded by the laptop, which was connected to the RF generator via RS-232 interface.

Test Pulses to Quantify Cooling

Figure 2:
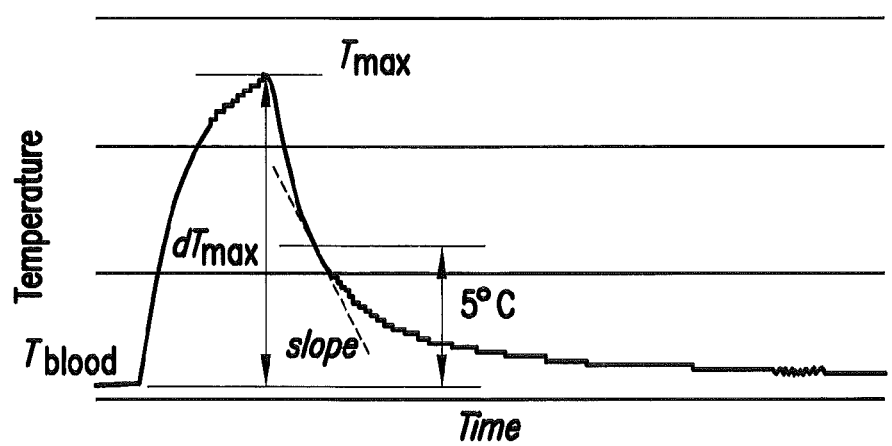
FIG. 2. Two parameters (dTmax and slope) are derived from application of a brief RF pulse.

Before commencing ablation, two RF test pulses were delivered to measure the two parameters shown in FIG. 2:
one pulse of constant power (15 W), for 5 s
one pulse of constant power (30 W), until tip temperature reached 43° C.

We waited 1 min in-between test pulses to allow tip temperature to return to baseline. Ablation parameters (T, P, Z) were recorded for 30 s from start of the test pulse. After application of the test pulse to the ablation catheter, RF power was diverted to electrodes placed in a beaker filled with saline; this was necessary since the RF generator doesn't report catheter tip temperature after RF power is shut down. We wrote software in Visual Basic 6.0 (Microsoft, Redmond, Wash.) to automate control of the switch for the two test pulses. The test pulses never resulted in tissue damage as confirmed in preliminary experiments.

From the temperature time-course of the first test pulse (15 W, 5 s) we measured the maximum change in tip temperature (dTmax) from the initial temperature. From the temperature time-course of the second test pulse (30 W until T=43° C.) we determined the slope of temperature decay at 5° C. over initial temperature (slope).

Since slope measurements are very sensitive to noise, we then used following method to determine slope:
approximate the temperature time-course over 1 s (centered around [Tblood+5° C.]) by 2nd order polynomial
determine slope of 2nd order polynomial at [Tblood+5° C.]
Customized software written in Matlab 6.5 (Mathworks, Natick, Mass.) was used to automate the slope measurements.

Ablation Protocol

Figure 6:
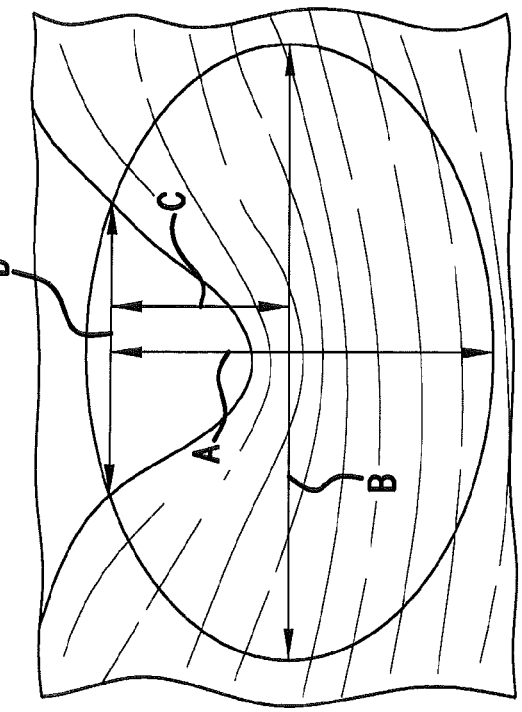
FIG. 6. Measurement of lesion dimensions.

After application of the test pulses, we performed temperature-controlled ablation for 60 sec. at a target temperature of 65° C. After the ablation was complete, the tissue sample was removed and cut through the center of the lesion perpendicular to the endocardial surface. Pictures of each lesion were taken with a digital camera (Canon PowerShot A510), and downloaded to a computer. We approximated the lesion boundary by an ellipsoid with image processing software (Paint Shop Pro 5.0). We then used the software ImageJ (available from NIH) to determine lesion dimensions (measurements A, B, C, D, see FIG. 6). A equals depth, B equals width, C equals depth at maximum width, and D equals width at endocardial surface. From these dimensions we estimated lesion volume using the equation for a partial oblate ellipsoid:

$$V = \frac{\pi}{12}(2AB^2 + CD^2) \quad (3)$$

Data Analysis

We performed a student's t-test to compare lesion dimensions (depth, width and volume) at different flow rates. Similarly, we compared the two variables $dT_{max}$ and slope at different flow rates. We considered significance at p<0.05. We performed linear regression analysis between:

$dT_{max}$ and lesion dimensions (depth, width and volume)

slope and lesion dimensions (depth, width and volume)

flow rate and lesion dimensions (depth, width and volume)

From the linear regression equations for the two variables $dT_{max}$ and slope, we determined the error with which these variables were able to predict lesion width and depth. For each lesion, we determined deviation of width and depth from the estimates according to the linear regression equations (absolute error), and divided by actual depth and width (relative error). We report average and maximum error.

Results

Figure 7:
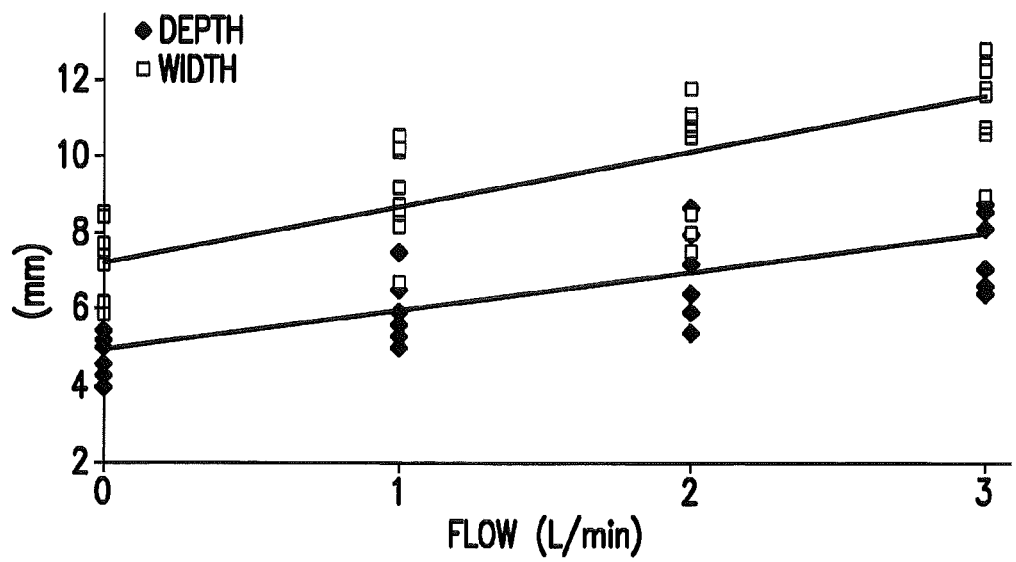
FIG. 7. Lesion depth (A) and width (B) at different flow rates, with linear approximation.

We found that lesion dimensions changed significantly with flow rate (FIG. 7). Lesions were smallest without flow (4.49 mm depth, 6.76 mm width, 56.44 mm³ volume), and largest at the highest flow rate of 3 L/min (7.55 mm depth, 11.32 mm width, 260.34 mm³ volume). Both parameters ($dT_{max}$, slope) exhibited linear relationships with both lesion width and depth (see FIG. 8). The parameter $dT_{max}$ showed strong correlation with both lesion width ($R^2=0.57$) and lesion depth ($R^2=0.68$); the parameter slope correlated slightly weaker with lesion width ($R^2=0.52$) and lesion depth ($R^2=0.62$). The parameter $dT_{max}$ allowed estimation of lesion width and depth with average error of 13.31% (1.14 mm) and 11.16% (0.67 mm), respectively. Again, parameter slope performed slightly worse with average error for lesion width and depth of 14.35% (1.22 mm) and 12.96% (0.78 mm), respectively.

For the parameter of depth, all comparisons of flow rates showed a significant difference between depth except between flow rates 2 and 3 L/min (see Table 3). For the parameter of width, all comparisons showed a significant difference except between flow rates 1 and 2 L/min. Finally, the parameter of volume showed a significant difference for all comparisons.

Figure 8A:
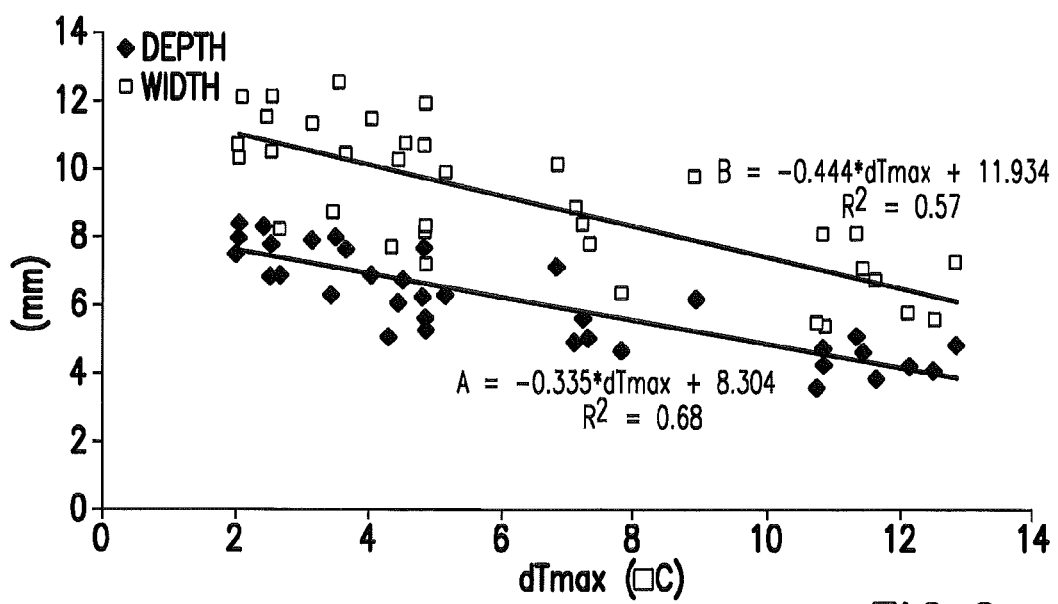
FIG. 8*a*. Lesion depth (A) and width (B) versus maximum temperature change (dTmax), with linear approximation.
Figure 8B:
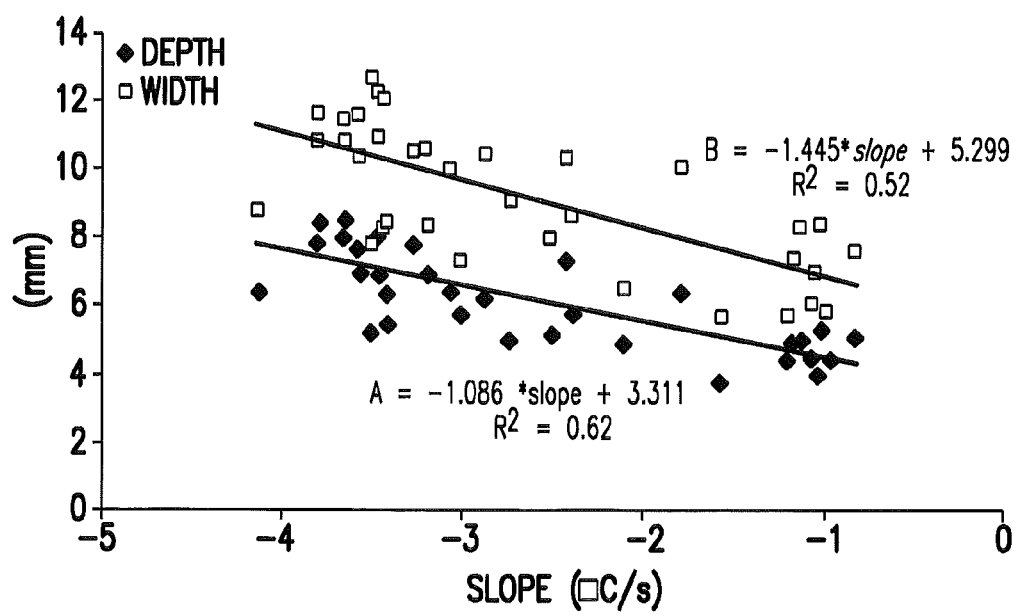
FIG. 8*b*. Lesion depth (A) and width (B) versus slope (slope), with linear approximation.

FIG. 10, Table 1 displays the electrode temperature, power, impedance, and lesion dimensions for each flow rate. FIGS. 7 and 8 show the dependence of depth and width to flow rate, dTmax, and slope. Linear relationships are given for depth and width for each graph. FIG. 11, Table 2 displays the average and maximum errors in the estimation of lesion depth and width using both maximum temperature change (dTmax) and slope (slope). FIG. 12, Table 3 displays the results of a statistical t-Test: Two-Sample Assuming Unequal Variances for each parameter. All flow rates were compared against one another to determine whether there was a significant difference between the means (p<0.05). p-values are given, and significance is denoted by '*'.

Discussion

Most clinical RF ablation systems for catheter treatment of cardiac arrhythmias employ temperature control. Typically, a sensor located in the electrode tip measures temperature and applied power is controlled to keep tip temperature constant (usually between 60 and 70° C.). A number of studies employing computer models, ex vivo experiments, and in vivo animal models, have demonstrated the dependence of RF lesion dimension generated on local convective cooling [1-5]. Embodiments of this invention comprise a quantitative and practical system to assess local convective cooling in vivo, and predict lesion size during clinical cases.

Local convective cooling can have a dramatic and significant effect on RF lesion size during temperature controlled ablation in the absence of power limitations. In our results, the greater the convective cooling was, the larger the lesion (see FIG. 10, Table 1, FIG. 7), confirming the findings of prior studies [1-4]. Embodiments of the invention show two methods to quantify convective cooling using brief pulses of RF power, both of which can be performed during any standard ablation procedure. Embodiments of the invention show that two parameters derived from the time-temperature relationship of the catheter tip temperature after the RF pulses, dTmax and slope, can be used to predict in vitro RF lesion size with reasonable accuracy under a variety of flow conditions.

Both parameters (dTmax, slope) exhibited linear relationships with both lesion width and depth (see FIG. 8), and showed a strong, negative correlation with lesion width and depth. The average error with which the parameters were able to estimate lesion width and depth are between about 0.7 and 1.2 mm (see FIG. 11, Table 2). The parameters are suited to aid the estimation of lesion dimensions under changing flow conditions.

Figure 9:
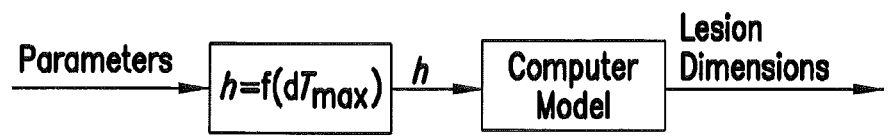
FIG. 9. The measured parameters (dTmax or slope) can be used to estimate convective cooling allowing use of computer models for accurate lesion estimation.

Certain embodiments of the invention correlated the measured parameters directly with lesion dimensions. Other embodiments of the invention can first use the parameters to estimate convective cooling, and then use this estimate together with other a-priori information from computer models to calculate lesion dimensions [4, 5]. A recently published article presents treatment planning software for cardiac RF catheter ablation which estimates lesion size depending on factors such as blood flow, ablation time, and target temperature [5]. However, estimates of convective cooling had to be used in these models since no patient specific data were available. Ablation site, heart rate, stroke volume and other factors all affect convective cooling within the heart. Embodiments of this invention provide a patient and site-specific estimate of convective cooling, allowing the use of a computer model to provide more accurate estimates of lesion dimensions (FIG. 9). The brief RF pulse used in embodiments of the invention cause only a minor increase in procedural time and can be integrated in clinical RF generators. Further, since both the derived parameters are measured relative to initial temperature (Tblood), differences in body temperature among patients do not constitute an error source.

Actual conditions in the heart denote pulsatile flow. Pulsatile flow can make measurement of the parameters (dTmax, slope) more difficult, and can in some instances require more elaborate signal processing than used here. Also, insertion angle and depth vary in clinical practice, and can have a significant impact on both lesion sizes. Therefore, an estimate for catheter insertion depth or tissue contact can be incorporated into embodiments of the invention. Previous studies have proposed several methods to estimate catheter-tissue contact [12-14]. A parameter describing tissue contact can also be included in embodiments of the invention as an additional input parameter in computer models to estimate lesion dimensions with procedure-specific data on both flow conditions and tissue contact.

While various embodiments of the invention have been described, it may be apparent to those of ordinary skill in the art that many more embodiments and implementations are possible that are within the scope of this invention. For instance, application of embodiments of the invention can be made to cryo ablation by either heating or cooling the catheter briefly and measuring thermal dynamics. All such modifications are intended to be included within the scope of this disclosure and the present invention and protected by the following claims.

REFERENCES

[1] H. Cao, V. R. Vorperian, S. Tungjitkusolmun, J. Z. Tsai, D. Haemmerich, Y. B. Choy, and J. G. Webster, "Flow effect on lesion formation in RF cardiac catheter ablation," *IEEE Trans. Biomed. Eng.*, vol. 48, pp. 425-433, 2001.
[2] R. Mukherjee, P. Laohakunakorn, M. C. Welzig, K. S. Cowart, and J. P. Saul, "Counter intuitive relations between in vivo RF lesion size, power, and tip temperature," *J. Interv. Card. Electrophysiol.*, vol. 9, pp. 309-315, 2003.
[3] H. H. Petersen, X. Chen, A. Pietersen, J. H. Svendsen, and S. Haunso, "Lesion dimensions during temperature-controlled radiofrequency catheter ablation of left ventricular porcine myocardium: impact of ablation site, electrode size, and convective cooling," *Circulation*, vol. 99, pp. 319-325, 1999.
[4] S. Tungjitkusolmun, V. R. Vorperian, N. Bhavaraju, H. Cao, J. Z. Tsai, and J. G. Webster, "Guidelines for predicting lesion size at common endocardial locations during radio-frequency ablation," *IEEE Trans. Biomed. Eng.*, vol. 48, pp. 194-201, 2001.
[5] Y. C. Lai, Y. B. Choy, D. Haemmerich, V. R. Vorperian, and J. G. Webster, "Lesion size estimator of cardiac radiofrequency ablation at different common locations with different tip temperatures," *IEEE Trans. Biomed. Eng.*, vol. 51, pp. 1859-1864, 2004.
[6] M. K. Jain and P. D. Wolf, "A three-dimensional finite element model of radiofrequency ablation with blood flow and its experimental validation," *Ann. Biomed. Eng.*, vol. 28, pp. 1075-1084, 2000.
[7] S. Labonte, "Numerical model for radio-frequency ablation of the endocardium and its experimental validation," *IEEE Trans. Biomed. Eng.*, vol. 41, pp. 108-115, 1994.
[8] S. Nath, C. Lynch, 3rd, J. G. Whayne, and D. E. Haines, "Cellular electrophysiological effects of hyperthermia on isolated guinea pig papillary muscle. Implications for catheter ablation," *Circulation*, vol. 88, pp. 1826-1831, 1993.
[9] D. E. Haines and D. D. Watson, "Tissue heating during radiofrequency catheter ablation: a thermodynamic model and observations in isolated perfused and superfused canine right ventricular free wall," *Pacing Clin. Electrophysiol.*, vol. 12, pp. 962-976, 1989.
[10] J. Z. Tsai, J. A. Will, S. Hubbard-Van Stelle, H. Cao, S. Tungjitkusolmun, Y. B. Choy, D. Haemmerich, V. R. Vorperian, and J. G. Webster, "In-vivo measurement of swine myocardial resistivity," *IEEE Trans. Biomed. Eng.*, vol. 49, pp. 472-483, 2002.
[11] K. R. Foster and H. P. Schwan, "Dielectric properties of tissues and biological materials: a critical review," *Crit. Rev. Biomed. Eng.*, vol. 17, pp. 25-104, 1989.
[12] H. Cao, S. Tungjitkusolmun, Y. B. Choy, J. Z. Tsai, V. R. Vorperian, and J. G. Webster, "Using electrical impedance to predict catheter-endocardial contact during RF cardiac ablation," *IEEE Trans. Biomed. Eng.*, vol. 49, pp. 247-253, 2002.
[13] O. J. Eick, F. H. Wittkampf, T. Bronneberg, and B. Schumacher, "The LETR-Principle: a novel method to assess electrode-tissue contact in radiofrequency ablation," *J. Cardiovasc. Electrophysiol.*, vol. 9, pp. 1180-1185, 1998.
[14] J. M. Kalman, A. P. Fitzpatrick, J. E. Olgin, M. C. Chin, R. J. Lee, M. M. Scheinman, and M. D. Lesh, "Biophysical characteristics of radiofrequency lesion formation in vivo: dynamics of catheter tip-tissue contact evaluated by intracardiac echocardiography," *Am. Heart J.*, vol. 133, pp. 8-18, 1997.

We claim:

1. A method of cardiac ablation, comprising the steps of:
    introducing a radiofrequency catheter to a specific location in cardiac tissue, wherein the radiofrequency catheter is in contact with the cardiac tissue;
    applying energy to the specific location in the cardiac tissue by the radiofrequency catheter at a constant power for a predetermined time and terminating the application of energy upon the expiration of the predetermined time;
    with the radiofrequency catheter in place relative to specific location in the cardiac tissue, taking multiple measurements of temperature of the radiofrequency catheter during an interval that is subsequent to terminating the application of energy to the specific location in the cardiac tissue;
    calculating a predictive measurement of lesion size to be produced by a subsequent application of energy to the cardiac tissue, wherein the predictive measurement is a function of an observed rate of decline of temperature at the specific location in the cardiac tissue during the interval that is subsequent to terminating the application of energy to the cardiac tissue; and
    producing a lesion in cardiac tissue at the specific location in the cardiac tissue by subsequent application of energy to the specific location in the cardiac tissue, wherein the application of energy at the specific location in the cardiac tissue correlates to the predictive measurement calculated as the function of the observed rate of decline of temperature at the specific location in the cardiac tissue during the interval that is subsequent to terminating the application of energy to the specific location in the cardiac tissue.

2. The method of cardiac ablation described in claim 1, wherein the interval that is subsequent to terminating the application of energy to the cardiac tissue is defined by the decline from a first predetermined temperature to a second predetermined temperature.

3. The method of cardiac ablation described in claim 1, wherein the interval that is subsequent to terminating the application of energy to the cardiac tissue is defined by a predetermined time period.

4. The method of cardiac ablation described in claim 1, wherein, during the step of applying energy to the cardiac tissue by the radiofrequency catheter at the constant power for the predetermined period of time and terminating the application of energy upon the expiration of the predetermined time, the temperature of the radiofrequency catheter does not exceed fifty degrees Celsius (50° C.).

5. The method of cardiac ablation described in claim 1, wherein the predetermined time for applying energy to the cardiac tissue by the radiofrequency catheter is a time period that is less than a time period for the subsequent application of energy to the cardiac tissue to produce the lesion.

6. The method of cardiac ablation described in claim 1, wherein the predictive measurement of lesion size is determined by regression analysis.

7. The method of cardiac ablation described in claim 1, further comprising the step of measuring contact of the radiofrequency catheter with the specific location in the cardiac tissue and obtaining a measurement of the contact of the radiofrequency catheter with specific location in the cardiac tissue, and wherein the predictive measurement of lesion size is further a function of the measurement of the contact of the radiofrequency catheter with the cardiac tissue.

8. The method of cardiac ablation described in claim 1, wherein the step of calculating a predictive measurement is performed by a computer.

9. The method of cardiac ablation described in claim 1, wherein the predictive measurement of lesion size comprises a depth and a width of predicted lesion size.

10. The method of cardiac ablation described in claim 1, wherein the temperature is measured at a tip of the radiofrequency catheter.

* * * * *